(12) United States Patent
Pryor

(10) Patent No.: US 7,799,067 B2
(45) Date of Patent: Sep. 21, 2010

(54) FLEXIBLE RESHEATHABLE STENT DESIGN

(75) Inventor: Jack Pryor, Windsor, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 11/760,111

(22) Filed: Jun. 8, 2007

(65) Prior Publication Data

US 2007/0233236 A1 Oct. 4, 2007

Related U.S. Application Data

(62) Division of application No. 10/911,040, filed on Aug. 3, 2004, now Pat. No. 7,240,516.

(51) Int. Cl.
 *A61F 2/06* (2006.01)
(52) U.S. Cl. ................................. 623/1.15
(58) Field of Classification Search ........ 623/1.11–1.22
 See application file for complete search history.

(56) References Cited

U.S. PATENT DOCUMENTS

| | | | |
|---|---|---|---|
| 5,695,516 A | 12/1997 | Fischell et al. | |
| 5,728,131 A | 3/1998 | Frantzen et al. | |
| 5,868,782 A | 2/1999 | Frantzen | |
| 5,922,020 A | 7/1999 | Klein | |
| 6,331,189 B1* | 12/2001 | Wolinsky et al. | 623/1.15 |
| 6,340,366 B2 | 1/2002 | Wijay | |
| 6,579,310 B1* | 6/2003 | Cox et al. | 623/1.16 |
| 6,623,518 B2 | 9/2003 | Thompson et al. | |
| 6,638,300 B1 | 10/2003 | Frantzen | |
| 6,669,723 B2 | 12/2003 | Killion et al. | |
| 2001/0044648 A1 | 11/2001 | Wolinsky et al. | |
| 2001/0047199 A1* | 11/2001 | Wijay | 623/1.15 |
| 2002/0055770 A1 | 5/2002 | Doran et al. | |
| 2003/0023301 A1 | 1/2003 | Cox et al. | |
| 2004/0088043 A1 | 5/2004 | Klein | |
| 2006/0149355 A1* | 7/2006 | Mitelberg et al. | 623/1.16 |
| 2007/0061003 A1 | 3/2007 | Shmulewitz et al. | |

FOREIGN PATENT DOCUMENTS

WO WO 01/87184 11/2001

* cited by examiner

*Primary Examiner*—Suzette J Gherbi
(74) *Attorney, Agent, or Firm*—Serge Hodgson

(57) ABSTRACT

A self-expanding stent includes capture segments including a first capture segment and a second capture segment. The first capture segment includes a first crown coupled to a first crown of the second capture segment and a second crown, where the second crown is spaced apart from an adjacent second crown of the second capture segment when the self-expanding stent is in a relaxed state, and further where the second crown of the first capture segment captures the adjacent second crown of the second capture segment when the self-expanding stent is in a radially compressed state.

5 Claims, 13 Drawing Sheets

FLEXIBLE RESHEATHABLE STENT DESIGN

RELATED APPLICATIONS

This application is a division of and claims the benefit of U.S. patent application Ser. No. 10/911,040 filed Aug. 3, 2004.

BACKGROUND OF THE INVENTION

1. Field of the Invention

The present invention relates to an intra-vascular device and method. More particularly, the present invention relates to a stent for treatment of intra-vascular diseases.

2. Description of the Related Art

In stent deployment systems, a self-expanding stent is restrained within a sheath. After positioning of the stent at the desired location via fluoroscopic guidance, the physician retracts the sheath to deploy the stent, i.e., to expose the stent and allow it to self-expand.

Recapturable stents allow the stent to be recaptured after deployment of the recapturable stent has been initiated. More particularly, if the recapturable stent jumps or is otherwise positioned incorrectly as the physician begins to retract the sheath, the physician simply reverses the direction of the sheath and advances the sheath back over the recapturable stent to recapture the stent within the sheath. After the recapturable stent has been recaptured, the physician repositions the recapturable stent at the desired location and retracts the sheath to re-deploy the stent.

However, the human anatomy is tortuous by nature. Thus, during guidance of the recapturable stent to the desired location, the recapturable stent is subjected to significant bending and flexing. A conventional recapturable stent has practical limits to the allowed amount of bending. Avoiding extreme bending of the recapturable stent limits the range of anatomical variation in which the recapturable stent can be used. Additionally, a conventional recapturable stent is relatively non-conformal thus further limiting the range of anatomical variation in which the recapturable stent can be used.

SUMMARY OF THE INVENTION

A self-expanding stent includes capture segments including a first capture segment and a second capture segment. The first capture segment includes a first crown coupled to a first crown of the second capture segment and a second crown, where the second crown is spaced apart from an adjacent second crown of the second capture segment when the self-expanding stent is in a relaxed state, and further where the second crown of the first capture segment captures the adjacent second crown of the second capture segment when the self-expanding stent is in a radially compressed state.

Generally, each capture segment of the stent captures the immediately adjacent distal capture segment in a fish scale effect when the stent is in the radially compressed state.

Since each capture segment of the stent captures the immediately adjacent distal capture segment, the stent does not have loose ends or other protrusions which might catch on the end of a sheath as the sheath is slid from a proximal end to a distal end of the stent. By forming the stent with an absence of any loose ends or other protrusions which can be caught by the end of the sheath, a partially retracted sheath can be advanced distally back over the exposed portion of the stent thus recapturing the stent.

Further, most of the crowns of each capture segment of the stent are not connected, i.e., are unconnected, to the adjacent crowns of the adjacent capture segments of the stent. Thus, the stent is relatively flexible and conformal.

Since the stent is relatively flexible, the stent can be significantly bent and flexed during guidance to the desired location thus maximizing the range of anatomical variation in which the stent can be used. Further, since the stent is relatively conformal, the stent conforms to a wide range of vessels thus further maximizing the range of anatomical variation in which the stent can be used.

The present invention is best understood by reference to the following detailed description when read in conjunction with the accompanying drawings.

BRIEF DESCRIPTION OF THE DRAWINGS

Common reference numerals are used throughout the drawings and detailed description to indicate like elements.

DETAILED DESCRIPTION

Figure 1:
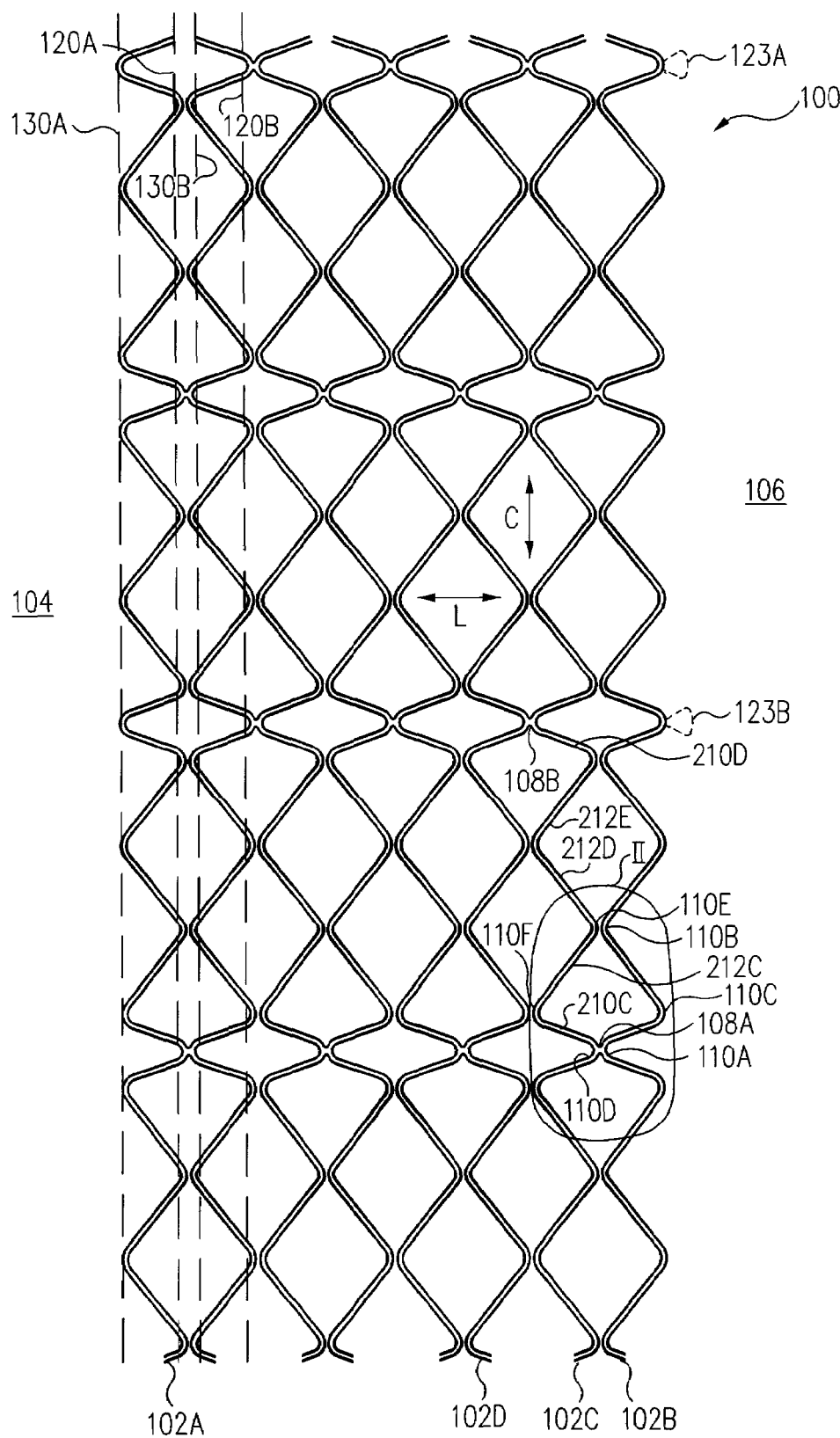
FIG. 1 is a laid flat plan view of an approximately half circumference of a stent in one embodiment according to the present invention.

FIG. 1 is a laid flat approximately half circumference plan view of a self-expanding stent 100 in an expanded configuration in one embodiment according to the present invention. Stent 100 includes a plurality of segments, sometimes called capture segments, including capture segments 102A, B, C, D, coupled to one another. Although eight capture segments are illustrated in FIG. 1, stent 100 can be formed with more or less than eight capture segments 102.

Illustratively, stent 100 is integral, i.e., is a single piece and not a plurality of separate pieces connected together. For example, stent 100 is formed by laser cutting a tubular piece of material. However, in an example, capture segments could be separate pieces, which are connected together, e.g., by welding.

Stent 100 includes a distal, e.g., first, end 104 and a proximal, e.g., second, end 106. Stent 100 extends longitudinally between distal end 104 and proximal end 106 along a longitudinal axis L, i.e., in the horizontal direction in the view of FIG. 1. A particular position along longitudinal axis L is sometimes called a longitudinal position.

In the laid flat plan view of FIG. 1, the direction perpendicular to longitudinal axis L is referred to as the circumferential axis C, i.e., is the vertical direction in the view of FIG. 1. A particular position along circumferential axis C is sometimes called a circumferential position.

A first capture segment 102A of the plurality of capture segments is located at and at its left circumferential edge is one of the elements that defines distal end 104. A second capture segment 102B of the plurality of capture segments is located at and at its right circumferential edge is one of the elements that defines proximal end 106. A third capture segment 102C of the plurality of capture segments is located directly adjacent to and coupled to capture segment 102B.

Each capture segment has a pattern, and this pattern is sometimes called a modified serpentine pattern. Capture segments are coupled to one another by connectors such as connectors 108A, B. Connectors extend between crowns such as crowns 110A and 110D, sometimes called peaks and valleys or minima and maxima, of the modified serpentine patterns of capture segments. Crowns define proximal edges such as proximal edges 120A, B and distal edges such as distal edges 130A, B of capture segments as indicated by the dashed lines.

As illustrated in FIG. 1, each fifth crown of a capture segment, e.g., capture segment 102C, is coupled by a connector to the corresponding fifth crown of the adjacent capture segment, e.g., capture segment 102B. This pattern of connectors to capture segments on either side of a capture segment having adjacent capture segments on either side is offset by two and one-half (2½) crowns between each adjacent capture segment. For example, the pattern of connectors between capture segment 102B and capture segment 102C is offset by two and one-half (2½) crowns relative to the pattern of connectors between capture segment 102C and a fourth capture segment 102D of the plurality of capture segments. However, other patterns of connectors can be used.

Since most of crowns of each capture segment are not connected, i.e., are unconnected, to the adjacent crowns of the adjacent capture segments of stent 100, stent 100 is relatively flexible and conformal.

Since stent 100 is relatively flexible, stent 100 can be significantly bent and flexed during guidance to the desired location thus maximizing the range of anatomical variation in which stent 100 can be used. Further, since stent 100 is relatively conformal, stent 100 conforms to a wide range of vessels thus further maximizing the range of anatomical variation in which stent 100 can be used.

Figure 2:
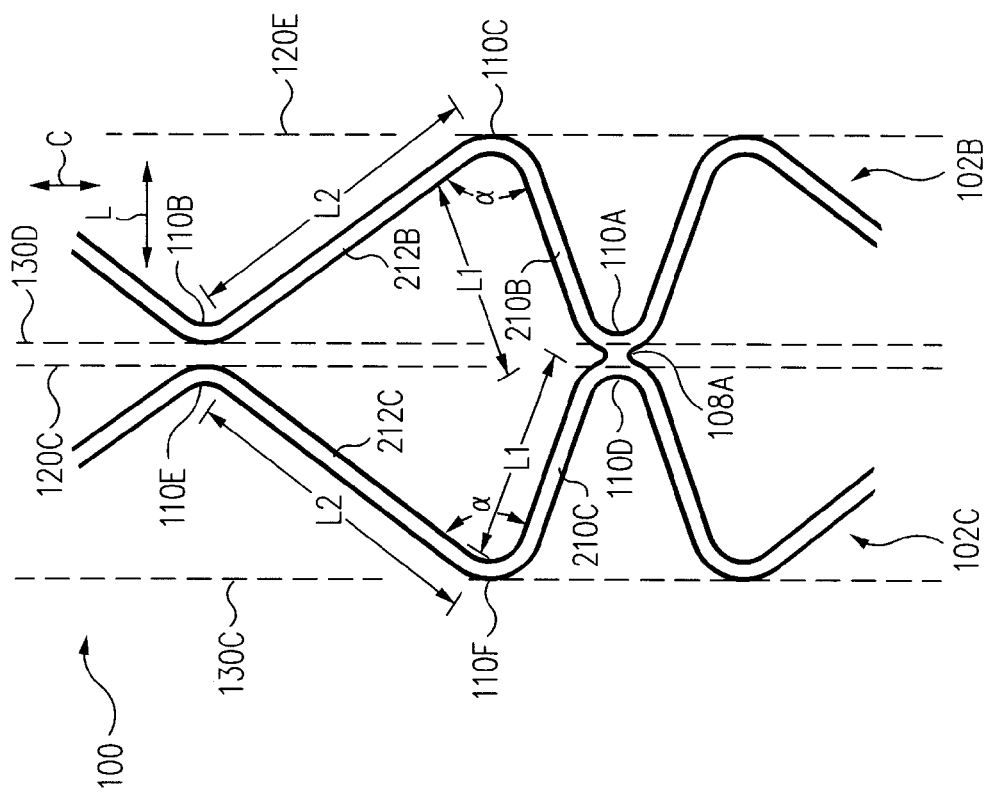
FIG. 2 is an enlarged laid flat plan view of region 11 of the stent of FIG. 1.

FIG. 2 is an enlarged laid flat plan view of a region II of stent 100 of FIG. 1. Referring now to FIG. 2, capture segment 102B includes a first crown 110A, a second crown 110B and a third crown 110C of the plurality of crowns of capture segment 102B. Crowns 110A and 110B define and are located at a distal edge 130D of capture segment 102B. Crown 110C defines and is located at a proximal edge 120E of capture segment 102B and between crowns 110A and 110B along circumferential axis C.

Capture segment 102B further includes a first arm 210B, sometimes called a short or straight arm, extending between and connecting crowns 110A and 110C. Capture segment 102B further includes a second arm 212B, sometimes called a long or straight arm, extending between and connecting crowns 110C and 110B.

A length L1 of first arm 210B, i.e., the distance between crowns 110A and 1110C, is less than a length L2 of second arm 212B, i.e., the distance between crowns 110C and 110B. Further, an angle α exists between first arm 210B and second arm 212B.

Capture segment 102C includes a first crown 110D, a second crown 110E and a third crown 110F of the plurality of crowns of capture segment 102C. Crowns 110D and 110E define and are located at a proximal edge 120C of capture segment 102C. Crown 110F defines and is located at a distal edge 130C of capture segment 102C and between crowns 110D and 110E along circumferential axis C.

Capture segment 102C further includes a first arm 210C extending between and connecting crowns 110D and 110F. Capture segment 102C further includes a second arm 212C extending between and connecting crowns 110F and 110E.

A length L1 of first arm 210C, i.e., the distance between crowns 110D and 110F, is less than a length L2 of second arm 212C, i.e., the distance between crowns 110F and 110E. Further, an angle α exists between first arm 210C and second arm 212C. In this example, capture segment 102C is a mirror image of capture segment 102B.

Crown 110A of capture segment 102B is connected to crown 110D of capture segment 102C by a first connector 108A of the plurality of connectors.

Figure 3:
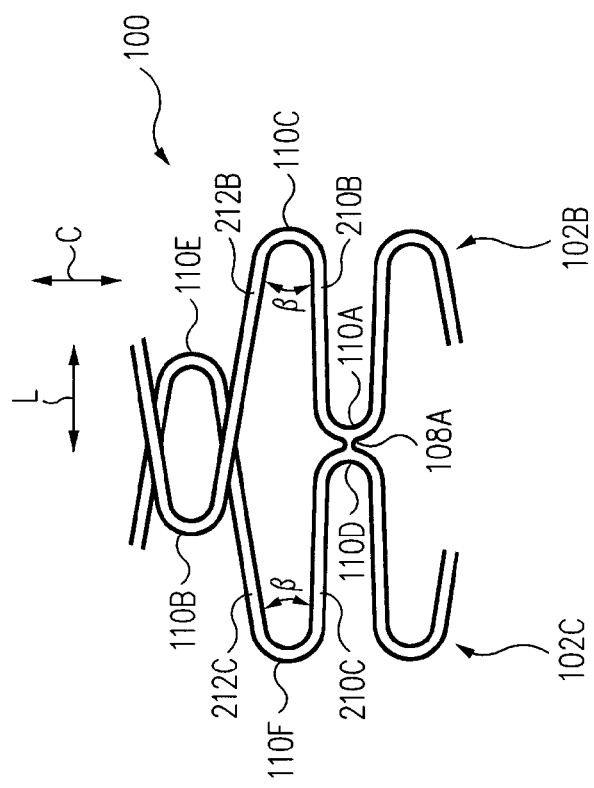
FIG. 3 is an enlarged laid flat plan view of the stent elements of region 11 of the stent of FIG. 1 after the stent has been radially compressed.

FIG. 3 is an enlarged laid flat plan view of the region II of stent 100 of FIG. 1 after stent 100 has been radially compressed, e.g., after stent 100 has been crimped or loaded into a sheath. More particularly, in the laid flat plan view of FIG. 3, stent 100 has been compressed along circumferential axis C.

Referring now to FIGS. 2 and 3 together, since crown 110A is coupled to crown 110D by connector 108A, crowns 110A, 110D remain at the same longitudinal positions relative to one another both when stent 100 is in its relaxed (expanded) configuration (position) as shown in FIG. 2 and when stent 100 is radially compressed (FIG. 3). Stated another way, crowns 110A, 110D do not move relative to one another along longitudinal axis L during radial compression of stent 100.

However, crowns 110B and 110C move to different longitudinal positions as stent 100 in its relaxed configuration (position) as shown in FIG. 2 is radially compressed to its compressed configuration (FIG. 3). Stated another way, crowns 110B, 110C move along longitudinal axis L during radial compression of stent 100.

More particularly, crown 110C moves proximally, e.g., to the right in the view of FIG. 2, along longitudinal axis L during radial compression of stent 100. Further, crown 110B moves distally, e.g., to the left in the view of FIG. 2, along longitudinal axis L during radial compression of stent 100.

In addition, the angles α between first arms 210B, C and second arms 212B, C decrease during radial compression of stent 100. More particularly, angles β (FIG. 3) exist between first arms 210B, C and second arms 212B, C when stent 100 is radially compressed, angles β being less than angles α (FIG. 2) between first arms 210B, C and second arms 212B, C when stent 100 is in its relaxed (expanded/unconstrained) state.

As a result of the difference in lengths L1 and L2 of arms 210B, C and 212B, C, respectively, crown 110B moves distally a greater distance than crown 110C moves proximally during radial compression of stent 100. Specifically, crown 110B moves distally and over crown 110E of capture segment 102C as illustrated in FIG. 3 thus capturing crown 110E. For similar reasons, crown 110E moves proximally and under crown 110B further facilitating capture of crown 110E. In the above manner, capture segment 102B captures capture segment 102C. Generally, capture segment 102B captures capture segment 102C by overlapping over capture segment 102C and gaining control over capture segment 102C by the overlap.

Referring again to FIG. 1, moving from connector 108A to a connector 108B between crowns of capture segments 102C, 102D along circumferential axis C, i.e., vertically upwards in the view of FIG. 1, capture segment 102C is formed from a short arm 210C, three long arms 212C, D, E, and a short arm 210D. Each arm is coupled to the adjacent arm at a crown of capture segment 102C. This pattern of arms is repeated for capture segments between crowns which are connected by connectors.

Figure 4:
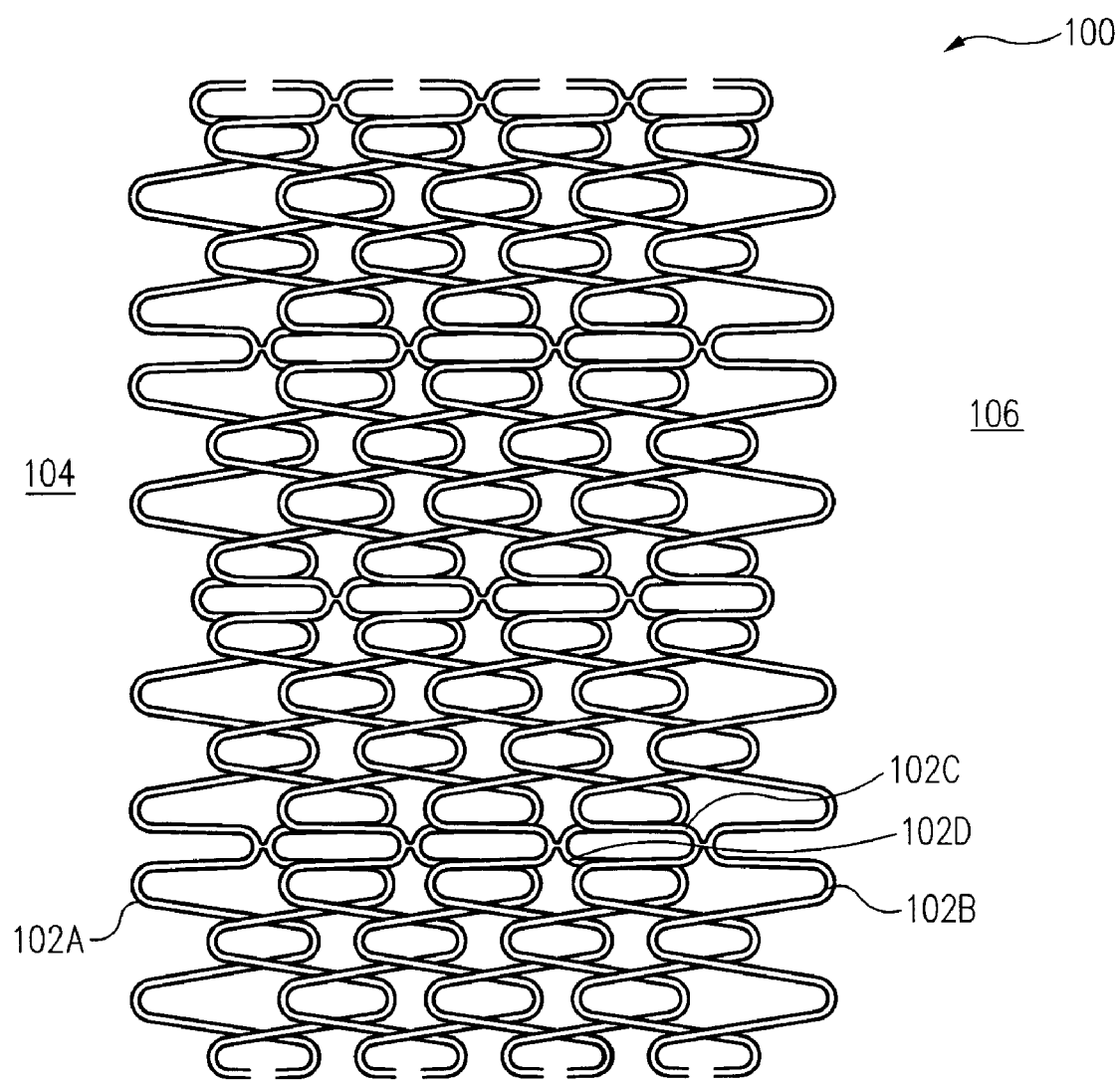
FIG. 4 is a laid flat plan view of the stent of FIG. 1 after the stent has been radially compressed.

FIG. 4 is a half circumferential laid flat plan view of stent 100 after stent 100 has been radially compressed. As illustrated in FIG. 4, generally, each capture segment of stent 100 captures the immediately adjacent distal capture segment in a manner similar to that discussed above with regards to FIGS. 2 and 3 in a fish scale effect.

Since each capture segment of stent 100 captures the immediately adjacent distal capture segment, stent 100 does not have any loose ends or other protrusions, which may hook or act as a stop when moving the sheath in one direction, relative to a sheath sliding from proximal end 106 to distal end 104 of stent 100. By forming stent 100 with an absence of any loose ends or other protrusions, which may hook or act as a stop when moving the sheath in one direction, a partially retracted sheath can be advanced distally back over the exposed portion of stent 100 thus recapturing stent 100.

To secure stent 100 in place during recapture, in one example, stent 100 is provided with one or more anchors such as anchors 123A, B, e.g., at proximal end 106, as indicated by the dashed lines in FIG. 1. Anchors are coupled to the inner member of the stent delivery system using any one of a number of techniques well known to those of skill in the art. For example, anchors are structures that fit into pockets of the inner member. When the sheath is retracted over and exposes the anchors, the expansion of the stent moves the anchors out of the pockets thus releasing the stent. See for example Thompson et al., U.S. Pat. No. 6,623,518. In one example, after partial or complete radial compression of stent 100, stent 100 is pulled from proximal end 106 to space capture segments out to eliminate the overlap between capture segments facilitating a minimal crossing profile.

Figure 5:
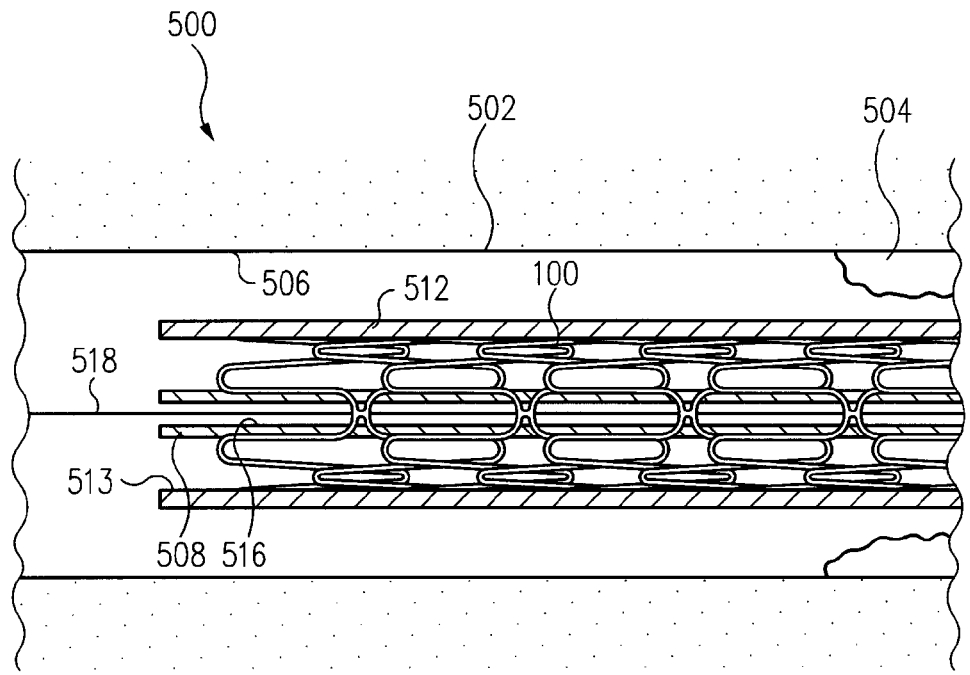
FIG. 5 is a modified partial cross-section view of a stent delivery system within a parent vessel of a patient adjacent to an occlusion.

FIG. 5 is a modified partial cross-section view of a stent delivery system 500 within a parent vessel 502 of a patient adjacent to an occlusion 504. Occlusion 504 occludes or completely blocks blood flow through parent vessel 502. Illustratively, occlusion 504 is plaque, thrombi, other deposits, emboli or other substances on an inner vessel wall 506 of parent vessel 502. Occlusion 504 reduces the blood carrying capacity of parent vessel 502. Left untreated, occlusion 504 could cause serious and permanent injury, or even death to the patient.

Delivery system 500 includes an inner member 508, stent 100, and a sheath 512. Although not illustrated, delivery system 500 includes other structures well known to those of skill in the art such as a handle.

Inner member 508, sometimes called a pushrod, is a hollow tubular member and includes a lumen 516, e.g., a guidewire lumen, through which a guidewire 518 extends.

Stent 100 is radially constrained by sheath 512. More particularly, prior to deployment, stent 100 is located within sheath 512. Sheath 512 includes a lumen 513 through which inner member 508 and guidewire 518 extend.

Figure 6:
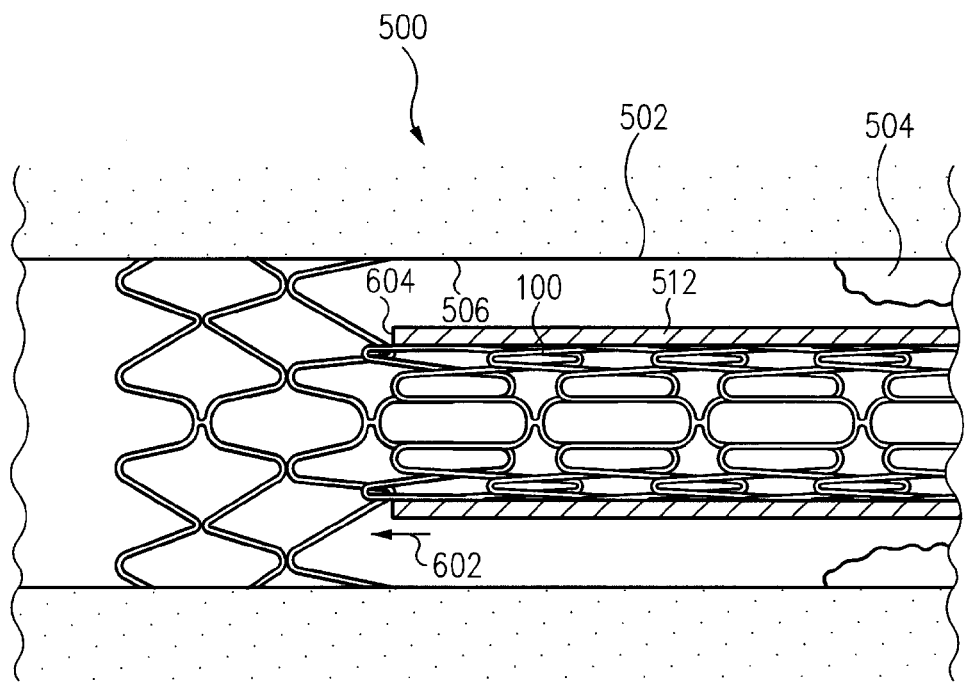
FIG. 6 is a modified partial cross-section view of the stent delivery system of FIG. 5 during deployment of a stent.
Figure 7:
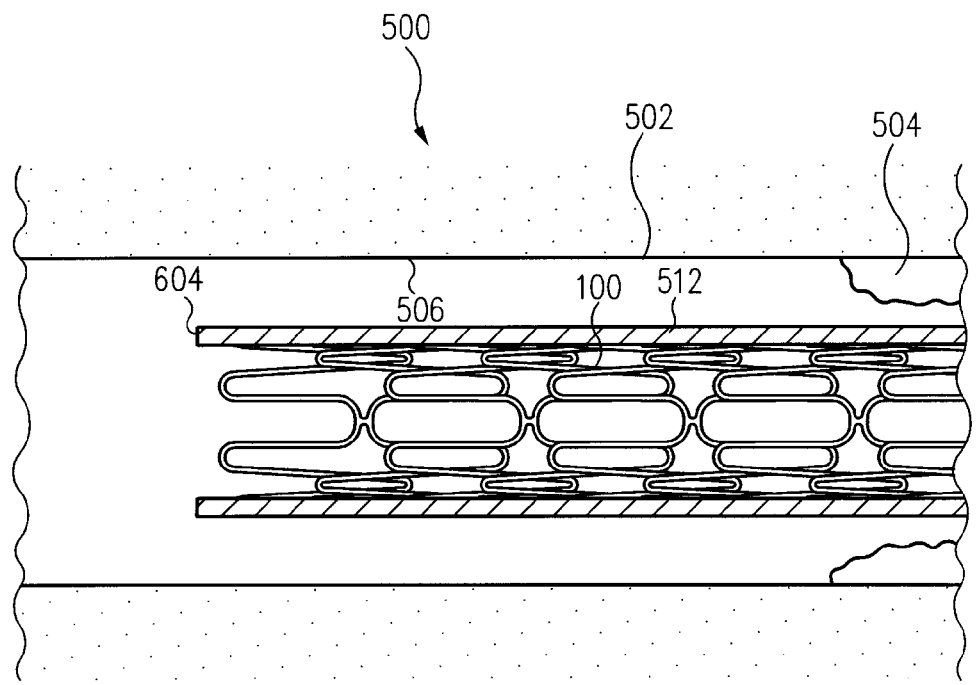
FIG. 7 is a modified partial cross-section view of the stent delivery system of FIG. 6 during recapture of the stent (advancement of a sheath over the stent)
Figure 8:
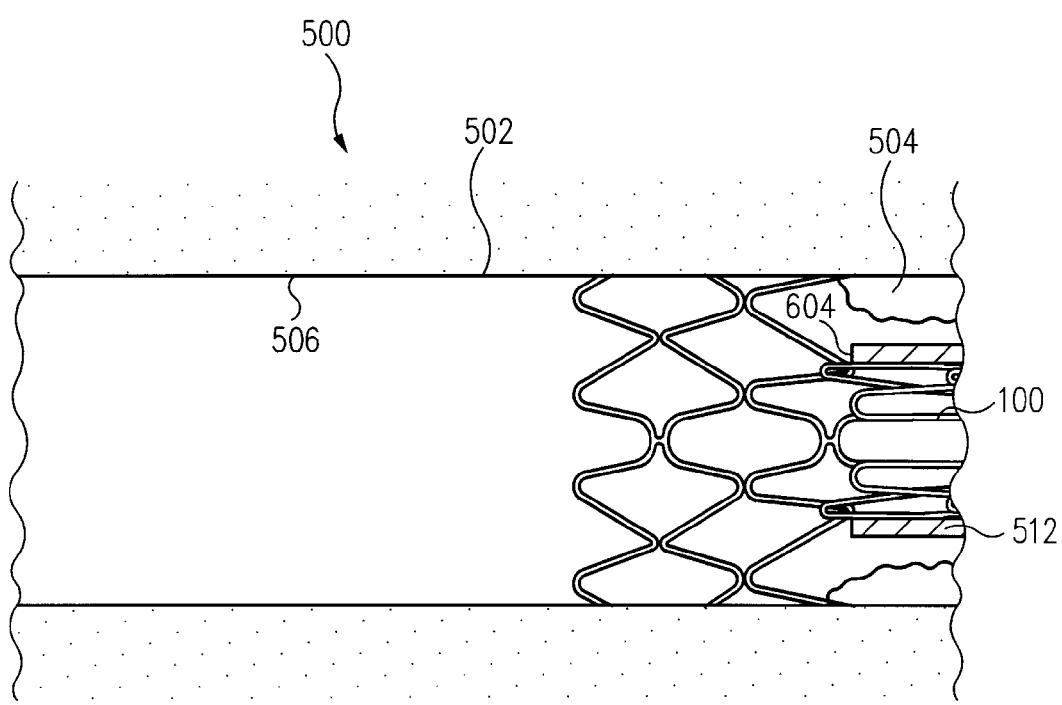
FIG. 8 is a modified partial cross-section view of the stent delivery system of FIG. 7 during re-deployment of the stent.

FIG. 6 is a modified partial cross-section view of stent delivery system 500 of FIG. 5 during deployment of stent 100. In FIGS. 6, 7, and 8, inner member 508 and guidewire 518 are not illustrated for clarity of presentation.

Referring now to FIGS. 5 and 6 together, to deploy stent 100, sheath 512 is retracted by the physician. As sheath 512 is retracted, the first few capture segments of stent 100, i.e., a portion of stent 100, are uncovered by sheath 512 and exposed. As a result, the first few capture segments of stent 100 self-expand into inner vessel wall 506 of parent vessel 502. Stent 100 is a self-expanding type stent, e.g., formed of a super elastic metal.

These first few capture segments of stent 100 are slowly and carefully deployed by the physician. This allows the physician to deploy the first few capture segments 102 of stent 100 and assess the position of stent 100 within parent vessel 502 and with respect to the location of the occlusion 504.

In the event that the positioning of stent 100 with respect to the location of the occlusion 504 is unsatisfactory, the physician can stop retraction of sheath 512. The physician can then reverse the direction of sheath 512, sometimes called advance the sheath 512, back over stent 100 to recapture stent 100 as illustrated below in FIG. 7.

FIG. 7 is a modified partial cross-section view of stent delivery system 500 of FIG. 6, stent 100 having been recaptured from the partial deployment shown in FIG. 6. Referring now to FIGS. 6 and 7 together, to recapture stent 100, sheath 512 is advanced by the physician in the direction of arrow 602 (FIG. 6). Generally, retraction means motion of sheath 512 in the proximal direction opposite of arrow 602 and advancement means motion of sheath 512 in the distal direction of arrow 602.

As sheath 512 is advanced, a distal end 604 of sheath 512 contacts and collapses capture segments of stent 100. Generally, as a capture segment is deployed or captured by sheath 512, the capture segment has a smaller diameter at the proximal end of the capture segment than at the distal end of the capture segment as shown in FIG. 6. Stated another way, the proximal end of the capture segment is more collapsed than the distal end of the capture segment.

As a result, as a capture segment is deployed or captured by sheath 512, the capture segment is funnel shaped. This facilitates the extension of the crowns of the capture segment over the crowns of the immediately distal capture segment. In one example, a stent is manufactured such that the crowns at the proximal end of each capture segment are angled or bent radially inwards to create/produce and initiate the funneling effect.

Sheath 512 is advanced until stent 100 is entirely covered by sheath 512 as shown in FIG. 7.

More particularly, as sheath 512 is advanced over stent 100, capture segments are sequentially radially compressed. As a result, crowns of a capture segment are advanced over crowns of the immediately adjacent distal capture segment as the capture segment is radially compressed by sheath 512 in a manner similar to that discussed above with regards to FIGS. 2 and 3. This sequential radial compression of capture segments by sheath 512 allows each capture segment to sequentially capture the immediately distal capture segment thus preventing sheath 512 from getting caught on stent 100 and allowing stent 100 to be recaptured.

Once stent 100 is covered by sheath 512, stent 100 is repositioned. Sheath 512 is then again retracted thus re-deploying stent 100 as shown in FIG. 8.

Figure 9:
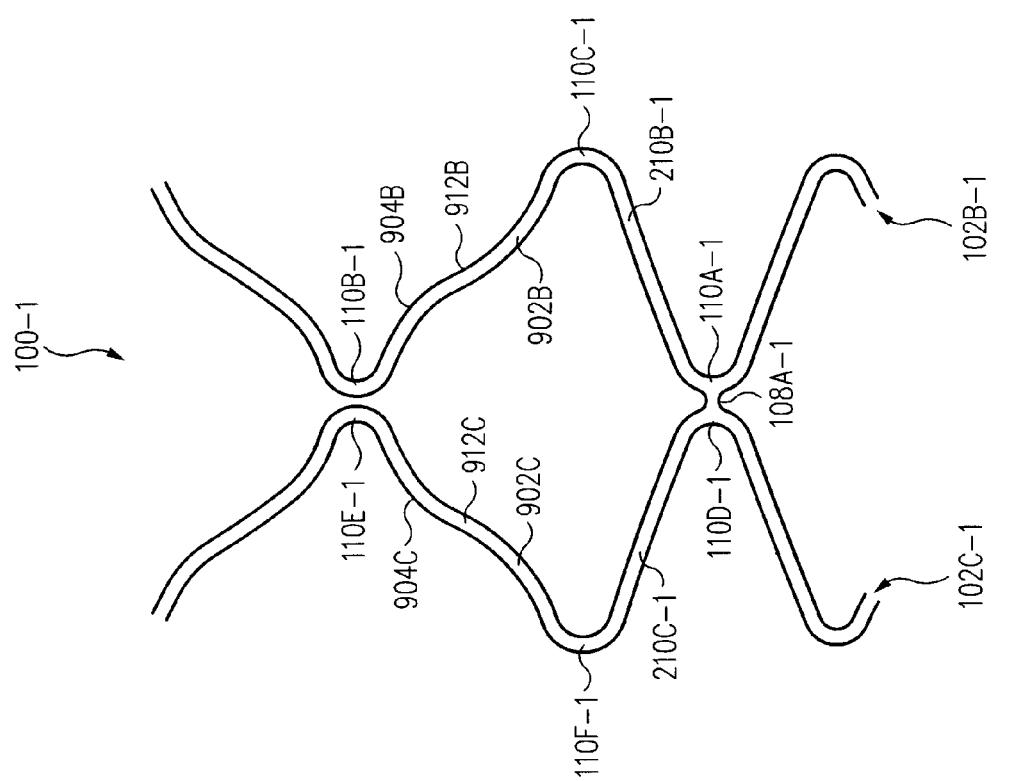

FIG. 9 is an enlarged laid flat plan view of a selected region of an alternative stent 100-1 in its relaxed state. Stent 100-1 of FIG. 9 is similar to stent 100 of FIG. 2 and only the significant differences are discussed below. More particularly, stent 100-1 of FIG. 9 includes capture segments 102B-1, 102C-1, a connector 108A-1, crowns 110A-1, 110B-1, 110C-1, 110D-1, 110E-1, 110F-1, first arms 210B-1, 210C-1 similar or identical to capture segments 102B, 102C, connector 108A, crowns 110A, 110B, 110C, 110D, 110E, 110F, first arms 210B, C of stent 100 of FIG. 2.

Referring now to FIGS. 2 and 9 together, instead of straight arms 212B, C of stent 100 as illustrated in FIG. 2, stent 100-1 includes curved arms 912B, C. Curved arms 912B, C include at least one curve, and, in this example, include first curves 902B, C and second opposite curves 904B, C, respectively. Generally, a stent such as stent 100-1 (FIG. 9) is formed with one set of curved arms 912B, C instead of straight arms 212B, C of stent 100 (FIG. 2).

Figure 10:
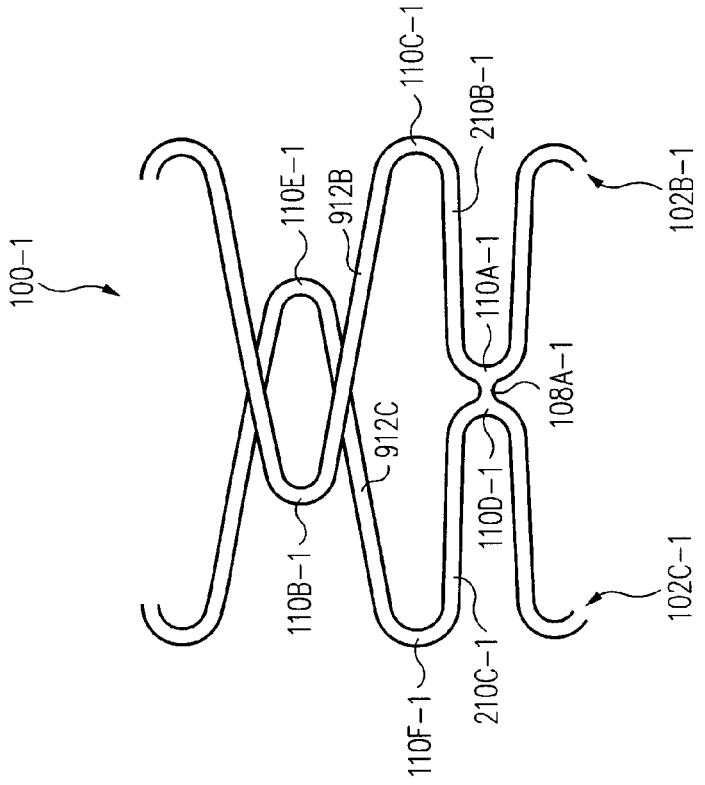
FIGS. 9 and 10 are enlarged laid flat plan views of another region of a stent in its relaxed and radially compressed state, respectively.

FIG. 10 is an enlarged laid flat plan view of the selected region of stent 100-1 of FIG. 9 after stent 100-1 has been radially compressed, e.g., after stent 100-1 has been crimped or loaded into a sheath.

Referring now to FIGS. 9 and 10 together, as stent 100-1 is radially compressed, curves 902B, C, 904B, C straighten, i.e., the radius of curves 902B, C, 904B, C increases or curves 902B, C, 904B, C become flat, thus lengthening curved arms 912B, C. This results in more distal motion of crown 110B-1 than if curved arm 912B was straight. In this manner, capture of crown 110E-1 of capture segment 102C-1 by crown 110B-1 of capture segment 102B-1 as illustrated in FIG. 10 is enhanced.

Figure 11:
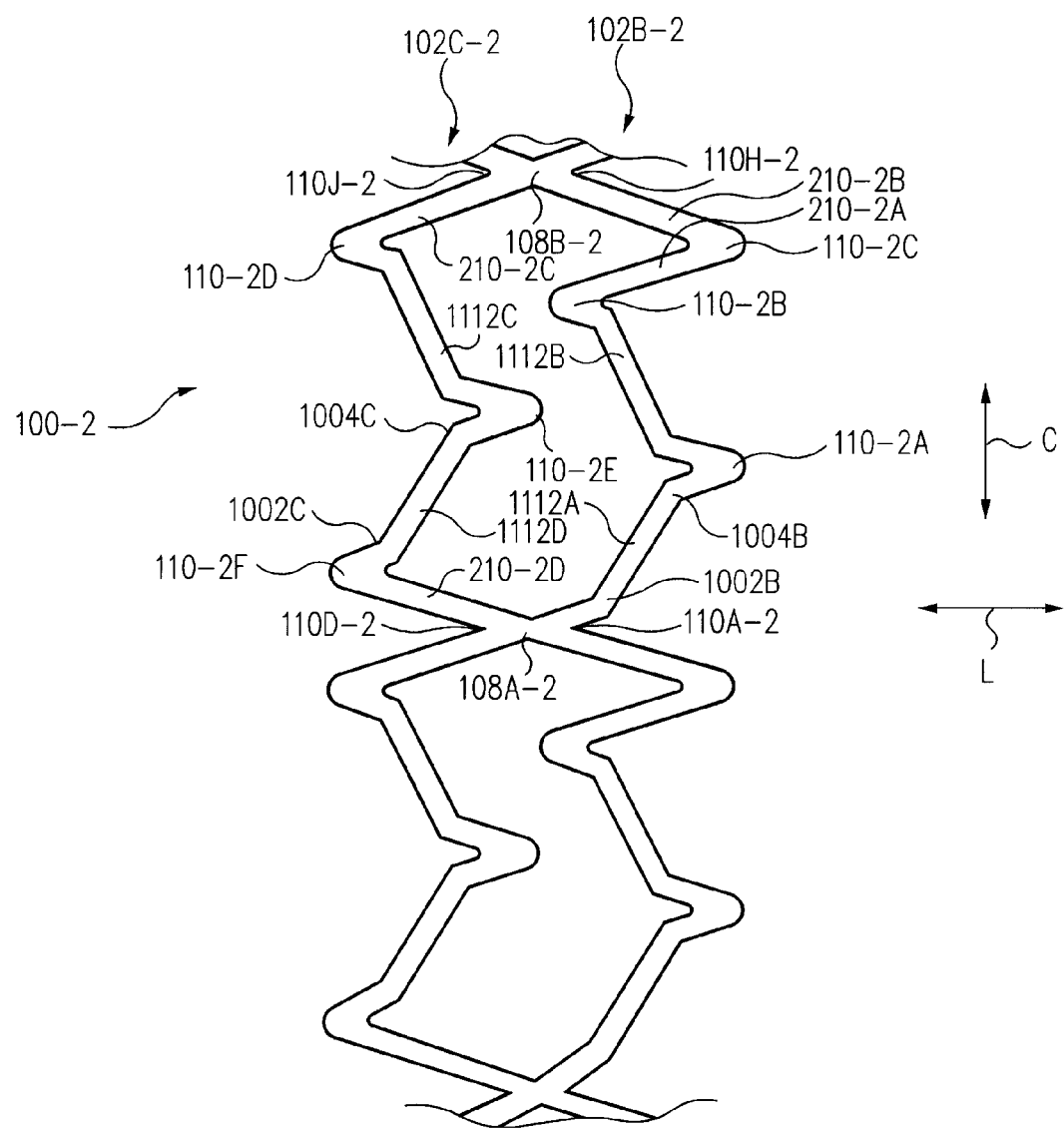
FIGS. 11 and 12 are enlarged laid flat plan views of another region of another stent in its relaxed and radially compressed state, respectively.

FIG. 11 is an enlarged laid flat plan view of a region of an alternative stent 100-2 in its relaxed state. Stent 100-2 of FIG. 11 is similar to stent 100 of FIG. 1 and only the significant differences are discussed below. More particularly, stent 100-2 of FIG. 11 include capture segments 102B-2, 102C-2, connectors, crowns, first arms similar or identical to capture segments 102B, 102C, connectors, crowns, first arms of stent 100 of FIG. 1.

Referring now to FIGS. 1 and 11 together, instead of straight arms of stent 100 as illustrated in FIG. 1, stent 100-2 includes bent arms such as bent arms 1112A, B, C, D. Bent arms include at least one bend, and in this example include first bends 1002B, C and second opposite bends 1004B, C.

Figure 12:
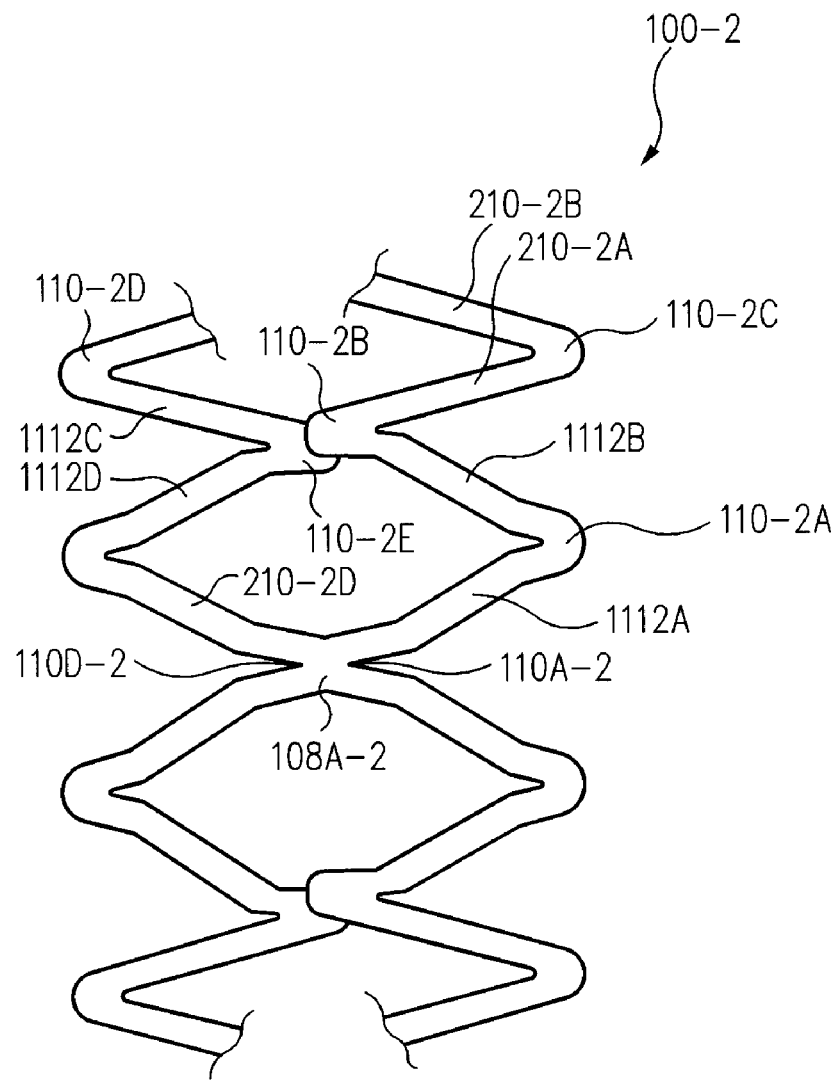

FIG. 12 is an enlarged laid flat plan view of the region of stent 100-2 of FIG. 11 after stent 100-2 has been radially compressed, e.g., after stent 100-2 has been crimped or loaded into a sheath.

Referring now to FIGS. 11 and 12 together, as stent 100-2 is radially compressed, bends 1002B, C, 1004B, C straighten, i.e., the angle of bends 1002B, C, 1004B, C increases or bends 1002B, C, 1004B, C become flat, thus lengthening bent arms 1112A, D. This results in more distal motion of crowns than if bent arms 1112A, D were straight. In this manner, capture of crowns of capture segment 102C-2 by crowns of capture segment 102B-2 as shown in FIG. 12 is enhanced.

Referring again to FIG. 11, capture segment 102C-2 is not a mirror image of capture segment 102B-2. More particularly, capture segment 102C-2 is identical to capture segment 102B-2 but is offset relative to capture segment 102B-2. Accordingly, capture segments are sometimes said to be in an identical offset pattern.

As shown in FIG. 11, a crown 110A-2 of capture segment 102B-2 is coupled to a crown 110D-2 of capture segment 102C-2 by a connector 108A-2. Further, a crown 110H-2 of capture segment 102B-2 is coupled to a crown 110J-2 of capture segment 102C-2 by a connector 108B-2.

Moving from connector 108A-2 to connector 108B-2 along circumferential axis C, i.e., vertically upwards in the view of FIG. 11, capture segment 102B-2 is formed from a bent arm 1112A (sometimes called a long arm), a bent arm 1112B, a straight arm 210-2A (sometimes called a short arm), and a straight arm 210-2B. Straight arms 210-2A, B have a length less than a length of bent arms 1112A, B. Each arm is coupled to the adjacent arm at a crown such as crowns 110-2A, B, C of capture segment 102B-2.

In contrast, moving from connector 108A-2 to connector 108B-2 along circumferential axis C, i.e., vertically upwards in the view of FIG. 11, capture segment 102C-2 is formed from a straight arm 210-2D, a bent arm 1112D, a bent arm 1112C, and a straight arm 210-2C. Each arm is coupled to the adjacent arm at a crown such as crowns 110-2D, E, F of capture segment 102C-2. This pattern of arms is repeated for capture segments 102B-2, 102C-2 and generally for capture segments between crowns which are connected by connectors.

Figure 13:
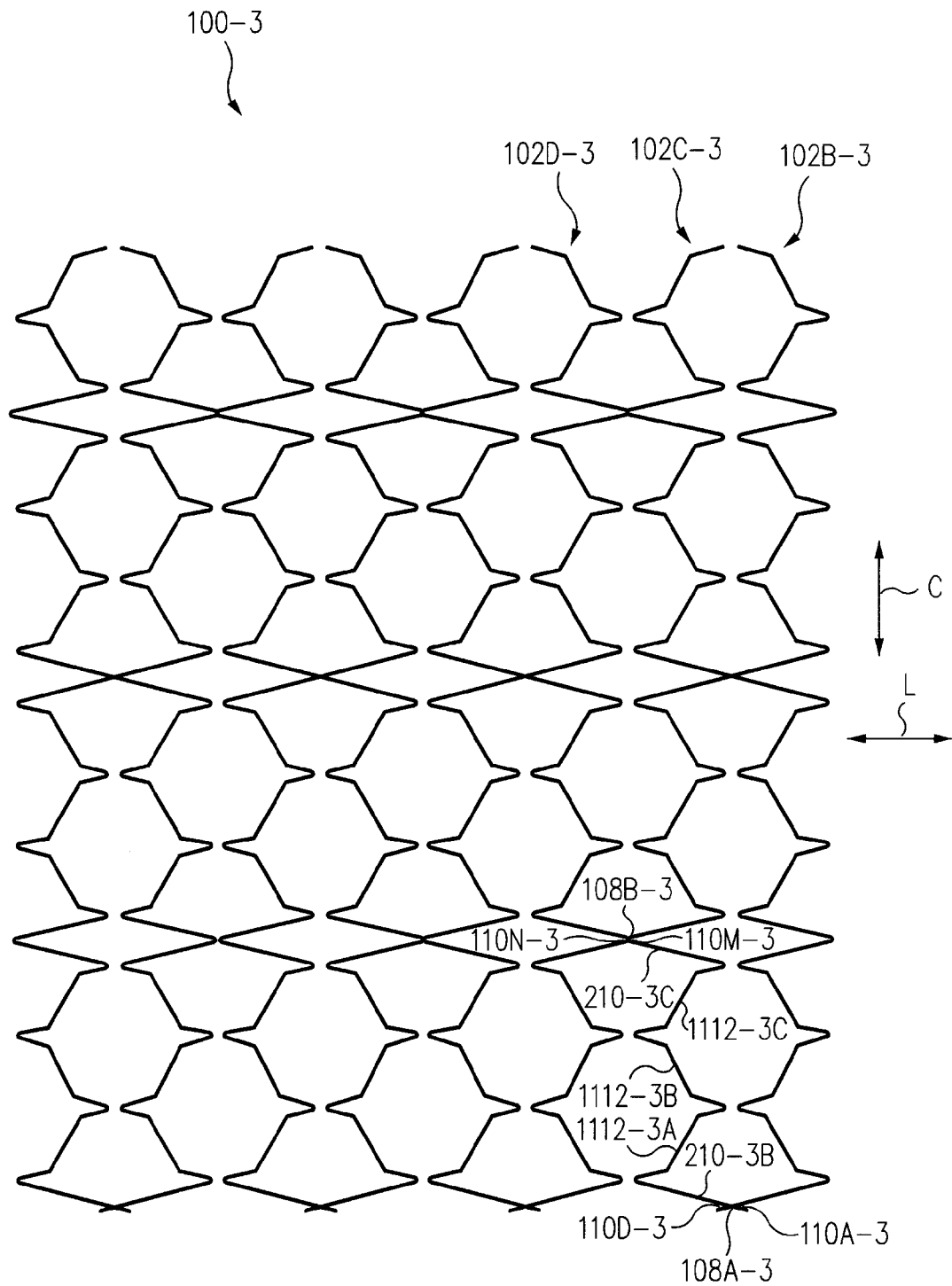
FIG. 13 is a laid flat approximately half circumference plan view of another stent in its relaxed state.

FIG. 13 is a laid flat plan view of a stent 100-3 in its relaxed state. Stent 100-3 of FIG. 13 is similar to stent 100 of FIG. 1 and only the significant differences are discussed below.

Referring to FIG. 13, a capture segment 102C-3 is a mirror image of a capture segment 102B-3. Generally, each capture segment is a mirror image of the directly adjacent capture segment.

A crown 110A-3 of capture segment 102B-3 is coupled to a crown 110D-3 of capture segment 102C-3 by a connector 108A-3. Further, a crown 110M-3 of capture segment 102C-3 is coupled to a crown 110N-3 of a capture segment 102D-3 by a connector 108B-3.

Moving from connector 108A-3 to connector 108B-3 along circumferential axis C, i.e., vertically upwards in the view of FIG. 13, capture segment 102C-3 is formed from a short arm 210-3B, three bent arms 1112-3A, B, C, and a short arm 210-3C. Each arm is coupled to the adjacent arm at a crown of capture segment 102C-3. This pattern of arms is repeated for capture segment between crowns, which are connected by connectors.

Figure 14:
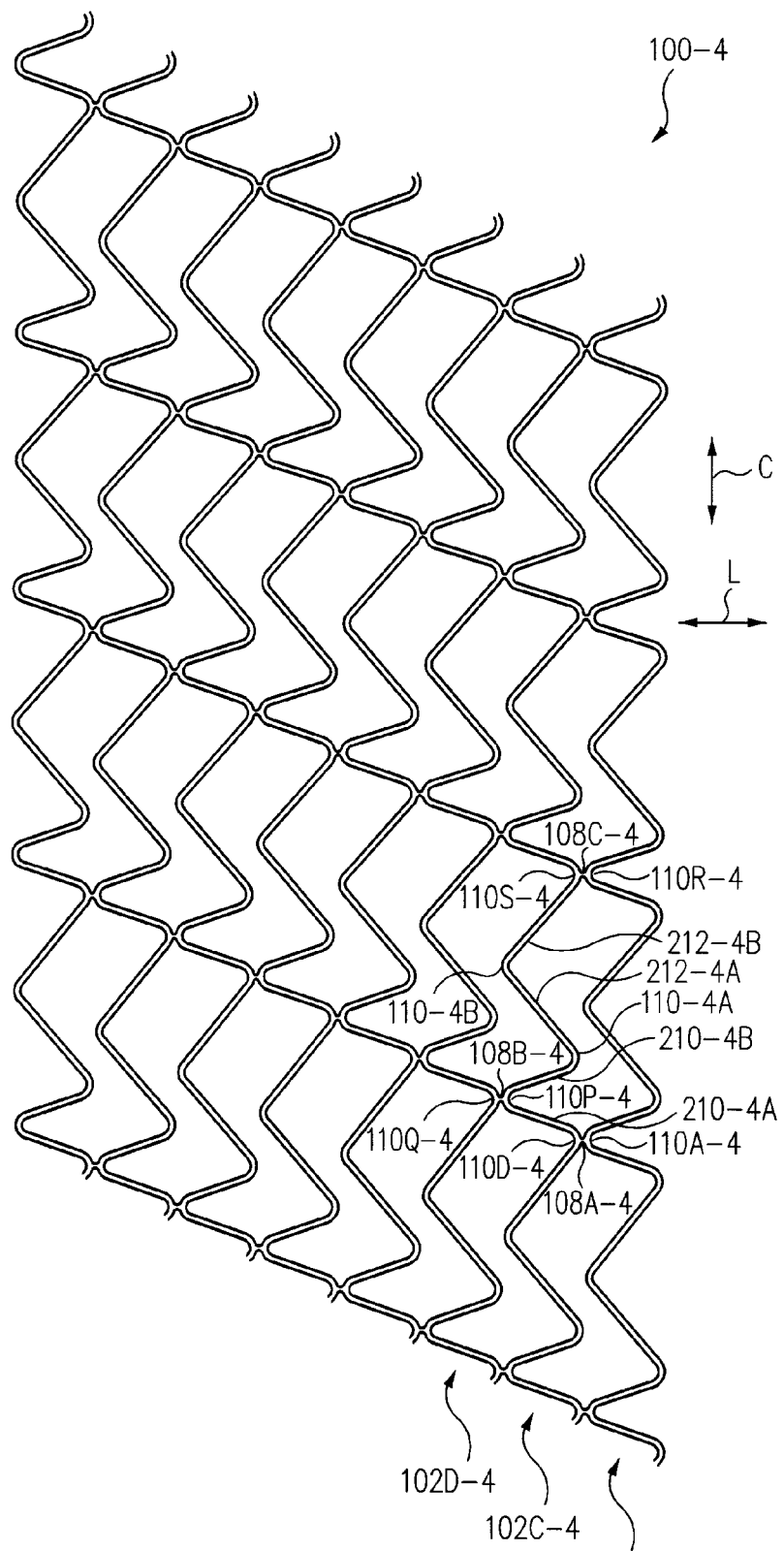
FIGS. 14 and 15 are laid flat approximately half circumference plan views of another stent in its relaxed and radially compressed state, respectively.

FIG. 14 is a laid flat plan view of a stent 100-4 in its relaxed state. Stent 100-4 of FIG. 14 is similar to stent 100 of FIG. 1 and only the significant differences are discussed below.

Referring now to FIG. 14, each capture segment of stent 100-4 is identical to the adjacent capture segment. However, each capture segment of stent 100-4 is offset relative to the adjacent capture segment. Accordingly, capture segments are sometimes said to be in an identical offset pattern.

A crown 110A-4 of a capture segment 102B-4 is coupled to a crown 110D-4 of a capture segment 102C-4 by a connector 108A-4. Further, a crown 110P-4 of capture segment 102C-4 is coupled to a crown 110Q-4 of a capture segment 102D-4 by a connector 108B-4. Still further, a crown 110R-4 of capture segment 102B-4 is coupled to a crown 110S-4 of capture segment 102C-2 by a connector 108C-4.

Moving from connector 108A-4 to connector 108B-4 along circumferential axis C, i.e., vertically upwards in the view of FIG. 14, capture segment 102C-4 is formed from a short arm 210-4A similar to arm 210C (FIG. 1).

Further, moving from connector 108B-4 to connector 108C-4 along circumferential axis C, i.e., vertically upwards in the view of FIG. 14, capture segment 102C-4 is formed from a short arm 210-4B, and two long arms 212-4A, B. Each arm is coupled to the adjacent arm at a crown such as crowns 110-4A, B of capture segment 102C-4.

This pattern of arms is repeated for capture segments between crowns, which are connected by connectors.

Figure 15:
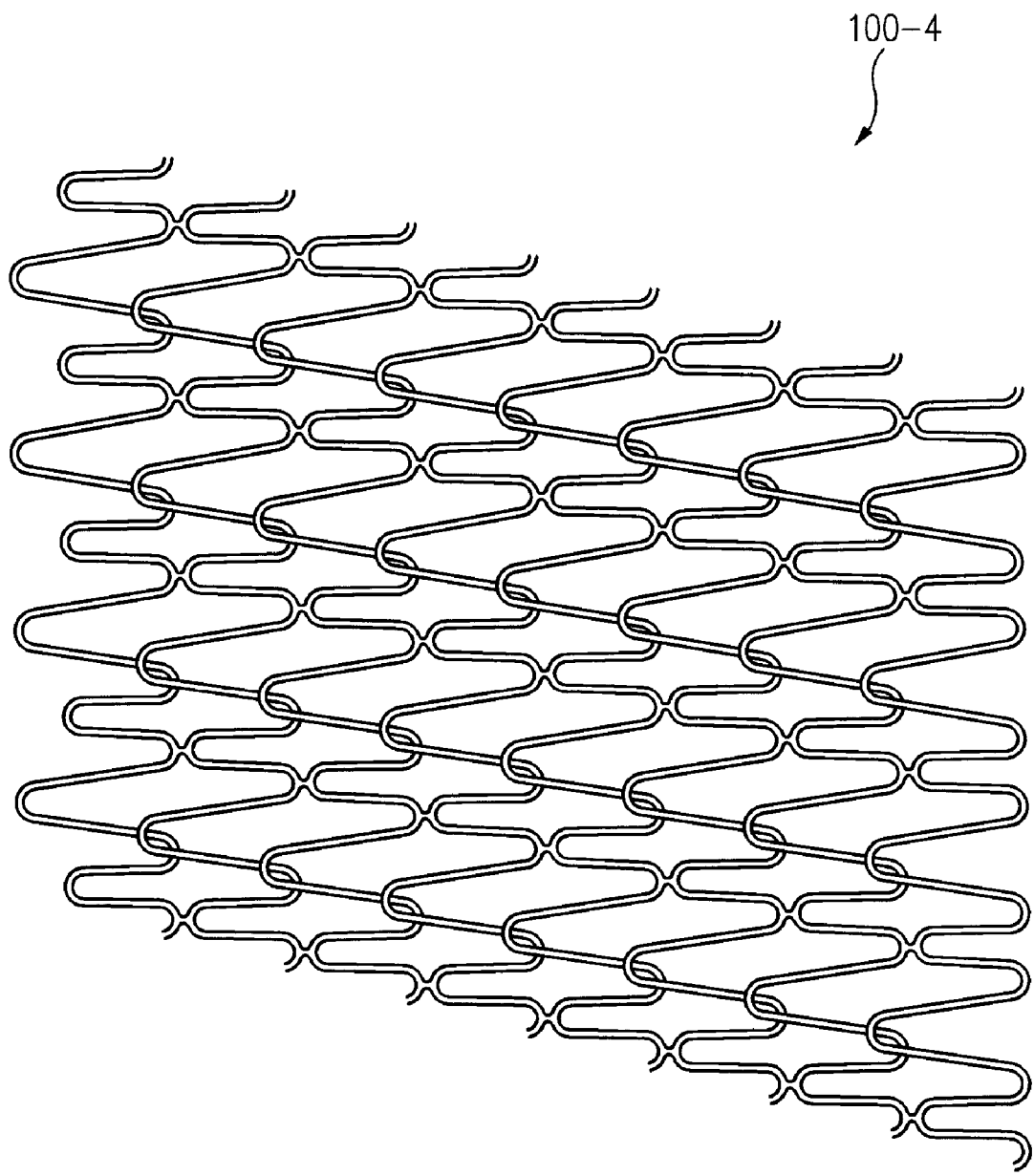

FIG. 15 is a laid flat plan view of stent 100-4 of FIG. 14 after stent 100-4 has been radially compressed. As illustrated in FIG. 15, generally, each capture segment of stent 100-4 captures the immediately adjacent distal capture segment in a manner similar to that discussed above with regards to FIGS. 2 and 3.

Figure 16:
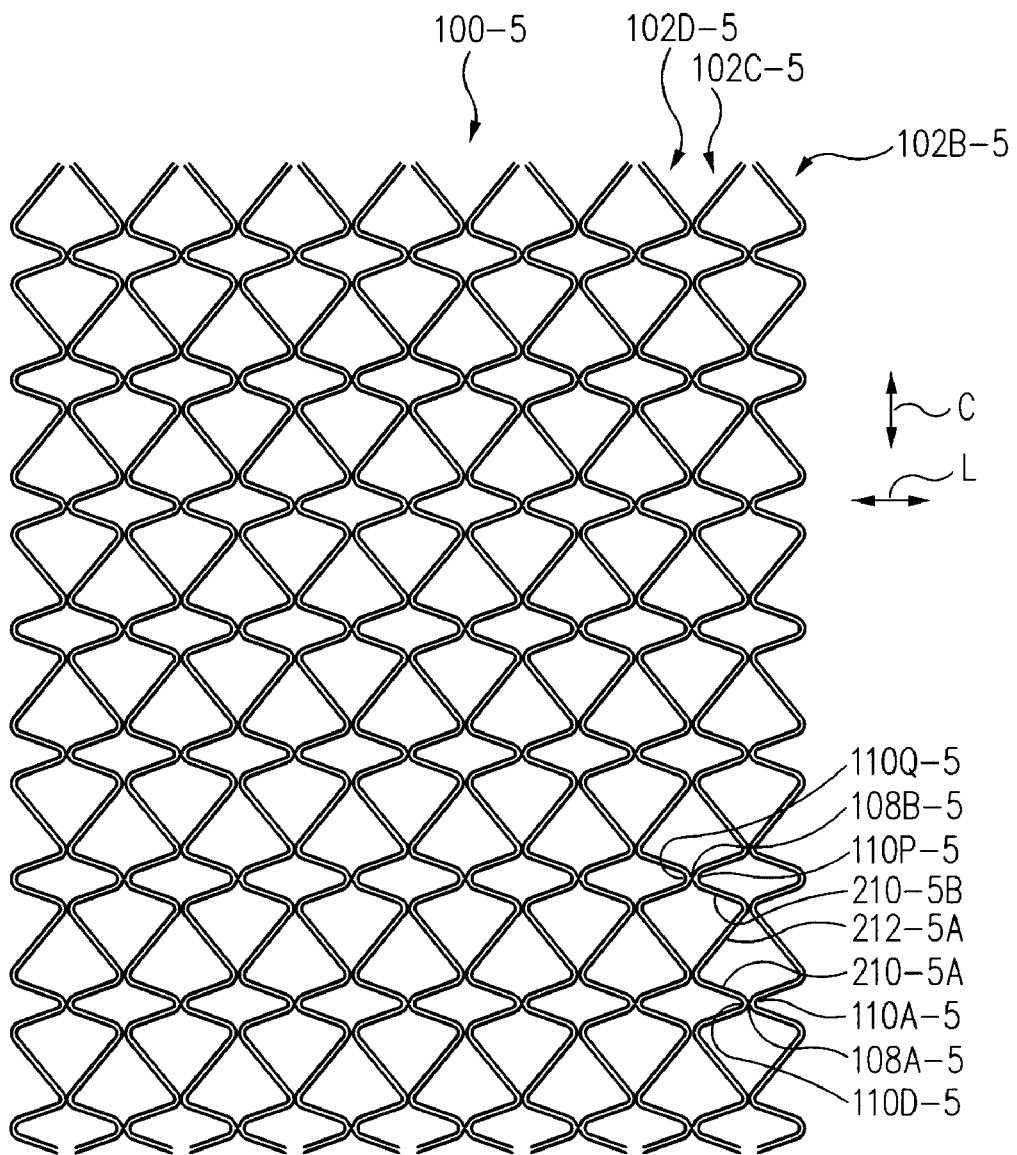
FIGS. 16 and 17 are laid flat approximately half circumference plan views of another stent in its relaxed and radially compressed state, respectively.

FIG. 16 is a laid flat plan view of a stent 100-5 in its relaxed state. Stent 100-5 of FIG. 16 is similar to stent 100 of FIG. 1 and only the significant differences are discussed below.

Referring now to FIG. 16, a capture segment 102C-5 is a mirror image of a capture segment 102B-5. Generally, each capture segment is a mirror image of the directly adjacent capture segment.

A crown 110A-5 of capture segment 102B-5 is coupled to a crown 110D-5 of capture segment 102C-5 by a connector 108A-5. Further, a crown 110P-5 of capture segment 102C-5 is coupled to a crown 110Q-5 of a capture segment 102D-5 by a connector 108B-5.

Moving from connector 108A-5 to connector 108B-5 along circumferential axis C, i.e., vertically upwards in the view of FIG. 16, capture segment 102C-5 is formed from a short arm 210-5A, a long arm 212-5A, and a short arm 210-5B. Each arm is coupled to the adjacent arm at a crown of capture segment 102C-5.

This pattern of arms is repeated for capture segments between crowns, which are connected by connectors.

Figure 17:
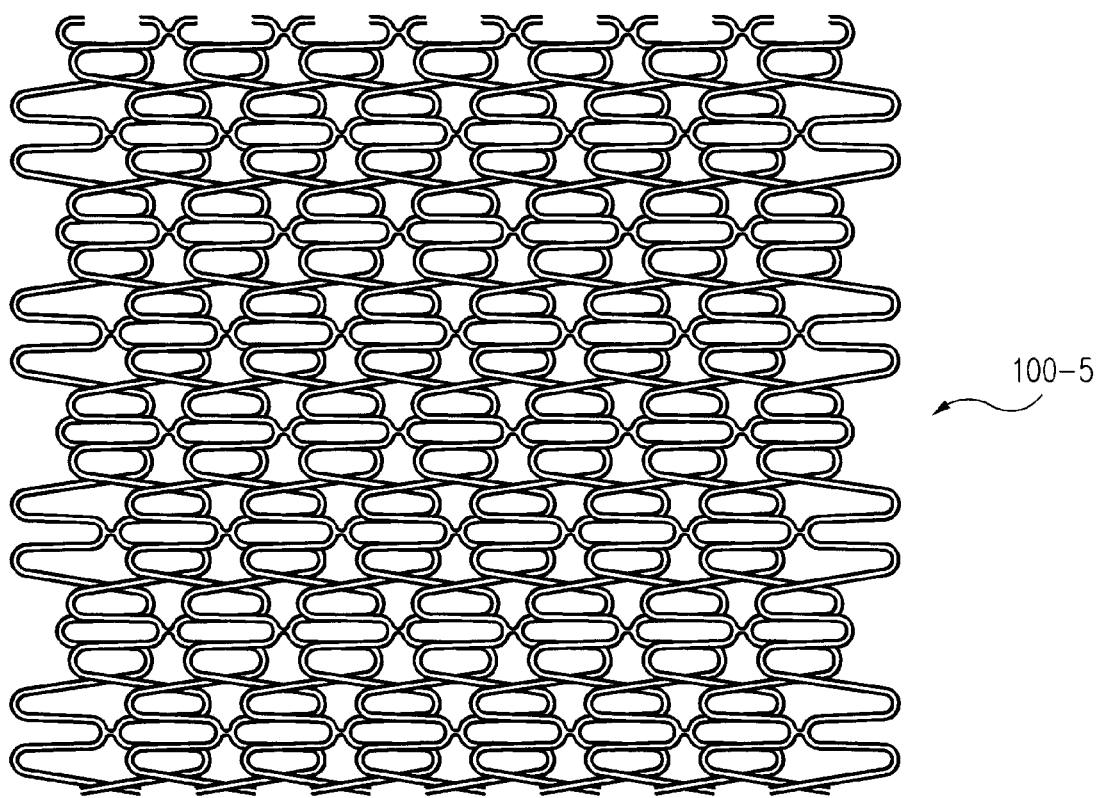

FIG. 17 is a laid flat plan view of stent 100-5 of FIG. 16 after stent 100-5 has been radially compressed. As illustrated in FIG. 17, generally, each capture segment of stent 100-5 captures the immediately adjacent distal capture segment in a manner similar to that discussed above with regards to FIGS. 2 and 3.

This disclosure provides exemplary embodiments of the present invention. The scope of the present invention is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A method comprising:
   initiating deployment of a self-expanding stent comprising capture segments;
   recapturing said self-expanding stent by sequentially collapsing said capture segments by a distal end of a sheath, wherein each of said capture segments captures the immediately adjacent distal capture segment during said recapturing;
   repositioning said self-expanding stent; and
   redeploying said self-expanding stent.

2. The method of claim 1 wherein said initiating deployment comprises retracting said sheath around said self-expanding stent.

3. The method of claim 1 wherein said recapturing comprises advancing said sheath over said self-expanding stent.

4. A method comprising:
   initiating deployment of a self-expanding stent comprising capture segments;
   recapturing said self-expanding stent by sequentially collapsing said capture segments into a funnel shape by a distal end of a sheath, wherein each of said capture segments captures the immediately adjacent distal capture segment during said recapturing;
   repositioning said self-expanding stent; and
   redeploying said self-expanding stent.

5. A method of recapturing a stent comprising:
   radially compressing said stent to cause a crown of a first segment of said stent by sequentially collapsing capture segments to move longitudinally relative to a crown of a second segment of said stent so that said first segment captures said second segment.

* * * * *